United States Patent [19]

Rossiter et al.

[11] Patent Number: 5,134,238
[45] Date of Patent: Jul. 28, 1992

[54] CHIRAL COPPER AMINE COMPLEXES

[75] Inventors: Bryant E. Rossiter, Provo, Utah; Masakatsu Eguchi, Stony Brook, N.Y.

[73] Assignee: Brigham Young University, Provo, Utah

[21] Appl. No.: 730,001

[22] Filed: Jul. 15, 1991

Related U.S. Application Data

[63] Continuation-in-part of Ser. No. 527,944, May 24, 1990, abandoned.

[51] Int. Cl.$^5$ .................... C07B 37/02; C07B 53/00; C07D 295/13
[52] U.S. Cl. ..................................... 546/11; 540/465; 540/541; 544/4; 544/64; 548/109; 548/402; 556/112; 568/351; 568/388
[58] Field of Search ....................... 546/11; 544/64, 4; 548/402, 109; 540/465, 541

[56] References Cited

PUBLICATIONS

Bertz et al., New Heterocuprates With Greatly Improved Thermal Stability, J. Am. Chem. Soc. 1982, 104, 5824–5826.
Bertz et al., Factors Governing the Thermal Stability of Organocopper Reagents,, Two New Classes of Heterocuprates With Greatly Improved Stability, J. Chem. Soc. Chem. 1982, 1030–1032.
Bertz et al., Asymmetric Induction with Amidocuprates, J. Org. Chem., 1986, 51, 4953–4959.
Dieter et al., Asymmetric Induction in the Conjugate Addition Reactions of Chiral Organo(hetero)cuprates, J. Am. Chem. Soc. 1987, 109, 2040–2046.
Rossiter et al., Enantioselective Conjugate Addition with Chiral Amidocuprates, Tetrahedron Letter, 1990, 31, 965–968.
Leyendecker et al., Fracteurs Controlant La Reconnaissance Enantioselective de La Chalcone Par Des Cuprates Chiraux, Nouveau Journal de Chimie, 1985, 9, 13–19.
Corey et al., Enantioselective Conjugate Addition of Nationally Designed Chiral Cuprate Reagents to 2-Cycloalkenones, J. Am. Chem. Soc., 1986, 108, 7114–7116.
Villacorta et al., Synthesis and Reactivity of Binuclear Tropocoronand and Related Organocopper (I) Complexes. Catalytic Enantioselective Conjugate Addition of Grignard Reagents to 2-Cyclohexen-1-one. J. Am. Chem. Soc., 1988, 110, 3175–3182.

Primary Examiner—Mark L. Berch
Attorney, Agent, or Firm—Delbert R. Phillips

[57] ABSTRACT

Disclosed herein is a class of chiral copper-amine complexes of the formula R(L*) CuLi in which L* is selected from:

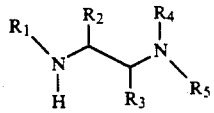

I

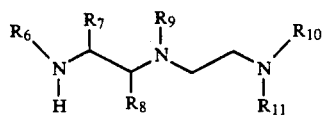

II

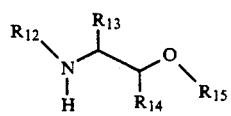

III

In this formula, R is a transferable ligand, which can be alkyl, aryl or aralkyl. M is a metal ion such as Li, Na, K, Cs, Rb, Be, Mg and other metal ions from the first two columns of the periodic table. $R_1$ is straight chain alkyl, $R_2$ is aryl or substituted aryl and $R_3$ and $R_4$ form a heterocyclic ring or a substituted heterocyclic ring with 4 to 8 members including oxygen and sulfur.

Such complexes react with $\alpha,\beta$-unsaturated ketones, aldehydes, esters and other carbonyl containing compounds such that R is transferred to the 3 position enantioselectively as shown below.

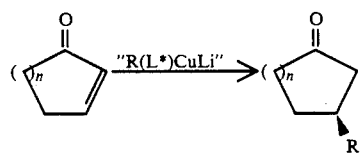

Such complexes react with $\alpha,\beta$-unsaturated ketones in the presence of trialkysilyl halides to give silyl enol ether in which R is substituted in the 3 position as shown below.

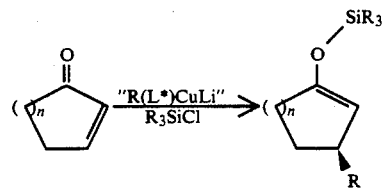

5 Claims, No Drawings

CHIRAL COPPER AMINE COMPLEXES

RELATED APPLICATIONS

This is a continuation in part of Ser. No. 07/527,944, filed May 24, 1990 now abandoned.

THE FIELD OF INVENTION

The present invention is concerned with a novel chiral inorganic complex derived from a copper(I) salt, an organometallic compound and a chiral metal amide. This invention also relates to the use of this chiral inorganic complex for enantioselective conjugate addition of organic radicals to $\alpha,\beta$-unsaturated carbonyl compounds. In addition, this invention relates to the performance of such transformations with and without triakylsilyl halides.

PRIOR ART

The manufacture of isomerically pure chiral organic molecules which are physiologically active is generally a difficult and expensive task. Most organic reactions which form chiral molecules do so with the formation of equal or nearly equal amounts of the possible stereoisomers. It is becoming increasingly clear that the isomers of physiologically active substances, such as drugs, do not, in general, have the same or even similar physiological activity. In some cases stereoisomers may even have harmful activity. For information on the FDA's perspective on stereoisomeric drug substances see: W. H. DeCamp *Chirality* 1989, 1, 2. It is therefore desireable for the sake of economy and consumer safety, that most chiral drug substances be synthesized in their stereoisomerically pure form.

A particularly useful reaction in organic chemistry is conjugate addition of organic moieties to $\alpha,\beta$-unsaturated carbonyl compounds using so-called cuprate reagents. The chemistry and utility of such reagents is reviewed in: G. H. Posner in "Organic Reactions" 1971, Vol 19 page 1. This reaction generally transfers a variety of organic moieties selectively, cleanly and in high chemical yield to the 3 position of such compounds. In so doing, a new stereogenic center is formed albeit as a racemate. The formula for such compounds is often represented as $R_nR_tCuLi$ where $R_n$ is the non-transferable ligand and $R_t$ is the transferable ligand. This is a stoichiometric formula i.e. it represents the relative ratios of components which go into making such complexes and does not necessarily represent a molecular formula. The actual molecular formula has not been determined at the present time. Such complexes in reality may be dimeric, trimeric etc. It has been shown that cuprate reagents are made up of four components; two organic ligands, copper(I) and a metal ion such as lithium. It has also been shown that only one of the organic ligands is transferred to the organic substrate. The transferring ligand must be a carbon moiety. The non-transferring ligand maybe a hydrocarbon moiety, alkoxide, sulfide or phosphide. It has been shown that when chiral molecules possessing such functional groups are used as non-transferable ligands, the conjugate addition reaction can occur enantioselectively with varying degrees of success. For a brief review of progress in developing enantioselective cuprates reagents see:

R. K. Dieter and M. Tokles *J. Am. Chem. Soc.* 1987, 109, 2040.

It has been demonstrated that a particularly good non-transferable ligand for this type of complex is an amide. For information on the use of amides as non-transferable ligands in cuprate reagents see:

a. S. H. Bertz, G. Dabbagh, G. M. Villacorta *J. Am. Chem. Soc.* 1982, 104, 5824.

b. S. H. Bertz; G. Dabbagh *J. Chem. Soc, Chem. Commun.* 1982, 1030.

Cuprates made from such substances are thermally stable and give high chemical yields. The present invention illustrates that when chiral amines with a particular structure profile are used as non-transferable ligands, highly enantioselective conjugate additions result.

BRIEF SUMMARY OF THE INVENTION

The present invention relates to chiral cuprate complexes whose stoichiometric formula is shown below.

$$R(L^*)CuM$$

In as much as the structure of such complexes has not yet been characterized, this complex will be referred to using the stoichiometric formula above. In this formula, R is an organic moiety capable of being transferred in the conjugate addition reaction. These organic radicals are selected from alkyl, aryl or aralkyl moieties which can be substituted by groups which would not interfere with the addition of the organic radicals to the $\alpha,\beta$-unsaturated carbonyl compounds. M is a metal ion such as Li, Na, K, Cs, Rb, Be, Mg and other metal ions from the first two columns of the periodic table. L*H is the chiral non-transferable ligand whose general formulas are shown below.

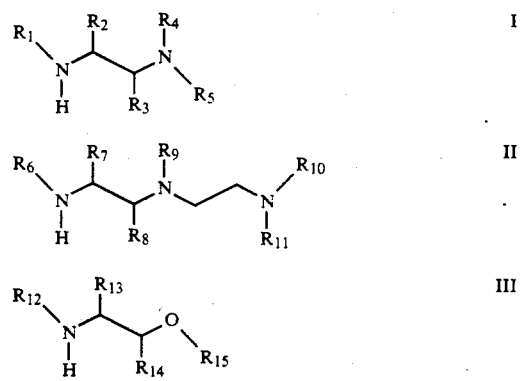

In formula I, $R_1$ and $R_2$ can be alkyl, aryl or aralkyl. $R_3$ can be H, alkyl, aryl or aralkyl. $R_4$ and $R_5$ can be alkyl, aryl or aralkyl. $R_4$ and $R_5$ can also form a heterocyclic ring of from 4–8 members including oxygen and sulfur such as piperidine, pyrrolidine or morpholine.

In formula II, $R_6$, $R_7$, and $R_9$ can be alkyl, aryl or aralkyl. $R_8$ can be H, alkyl, aryl or aralkyl. $R_{10}$ and $R_{11}$ can be alkyl, aryl or aralkyl. $R_{10}$ and $R_{11}$ can also form a heterocyclic ring of from 3–10 members including oxygen and sulfur containing no more than 2 hetero atoms such as piperidine, pyrrolidine, morpholine, perhydroazepine, perhydroazocine or 4-methylpiperdine.

In formula III, $R_{12}$, $R_{13}$ and $R_{15}$ can be alkyl, aryl, or aralkyl. $R_{14}$ can be H, alkyl, aryl or aralkyl.

In the preferred embodiment for formula I, $R_1$ is a straight chain alkyl from 1 to 12 carbon atoms and $R_2$ is aryl or substituted aryl, $R_3$ is H and $R_4$ and $R_5$ form a heterocyclic ring or substituted heterocyclic ring of 3 to 10 members, preferably $R_4$ and $R_5$ form a heterocyclic ring of 4–8 members containing no more than 2 hetero atoms consisting of N, O or S, such as piperidine, pyrrolidine, morpholine, perhydroazepine or perhydroazocine.

In the preferred embodiment for formula II, $R_6$ is a straight chain alkyl from 1 to 12 carbons, $R_7$ is aryl or substituted aryl, $R_8$ is H and $R_9$, $R_{10}$ and $R_{11}$ are straight chain alkyls from 1 to 12 carbons.

In the preferred embodiment of formula III, $R_{12}$ is a straight chain alkyl from 1 to 12 carbon atoms, $R_{13}$ is aryl or substituted aryl, $R_{14}$ is H, alkyl, aryl or aralkyl and $R_{15}$ is alkyl, aryl or aralkyl.

The present invention also relates to chiral cuprate complexes whose formula is shown below.

RCuM(L*-L*)MCuR

In this formula, R is any organic moiety capable of being transferred in the conjugate addition reaction preferably alkyl, aryl or aralkyl moieties. M is a metal ion such as Li, Na, K, Cs, Rb, Be, Mg and other metal ions from the first two columns of the periodic table. L*-L* is the chiral non-transferable ligand whose general formula is shown below.

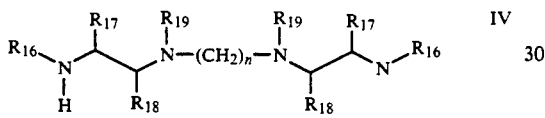

$R_{16}$, $R_{17}$ and $R_{19}$ are alkyl, aryl or aralkyl, $R_{18}$ is H, alkyl, aryl or aralkyl, and n is an integer from 1–20.

The above described complexes are formed as follows. In one flask under an inert atmosphere, the L*H or L*H-L*H amines, dissolved in a solvent such as diethyl ether, are deprotonated using one equivalent of a highly basic organometallic compound such as n-butyl lithium or phenyl lithium to give a solution of the corresponding metal amide. In a second flask an organocopper complex, CuR, is formed by reacting a copper(I) halide such as CuI suspended in a solvent such as diethyl ether with one equivalent of an organometallic compound such as n-butyl or phenyl lithium. The solution of metal amide is transferred by cannula and without contamination with air or moisture to the flask containing the organocopper compound, CuR. Alternatively, the complex can be formed by combining L*H or L*H-L*H in a flask with a copper(I) halide such as CuI in a solvent such as diethyl ether and treating this mixture with two equivalents of an organometallic compound such as n-butyl lithium or phenyl lithium. The organic moiety in the organocopper compound will ultimately be the transferable ligand. The L*H has one free proton attached to the secondary nitrogen to react with the strong base forming the complex. Likewise, the L*H-L*H only has two free protons attached to the secondary nitrogens to form the complex. The remainder of the nitrogens in the L*H and the L*H-L*H have no protons available for the formation of the complex.

The present invention also relates to the use of these reagents to perform enantioselective conjugate addition reactions using the complex L*(R)CuLi as exemplified in Scheme I.

Scheme I

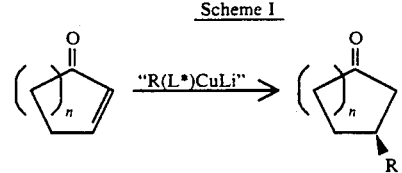

The present invention also relates to the use of these reagents to perform enantioselective conjugate addition reactions using the complex (R)CuM(L*-L*MCu(R) as exemplified in Scheme II.

Scheme II

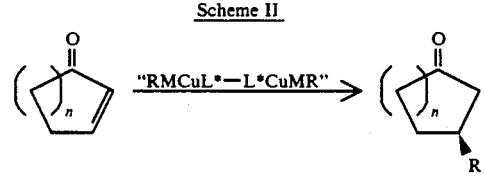

The present invention also relates to the use of such reagents in the presence of trialkylsilyl halides such that the product formed enantioselectively is an enantiomerically enriched silyl enol ether as illustrated in Scheme III.

Scheme II

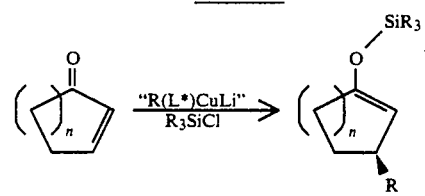

The present invention also relates to the use of such reagents in the presence of trialkylsilyl halides such that the product formed enantioselectively is an enantiomerically enriched silyl enolether as illustrated in Scheme IV.

Scheme IV

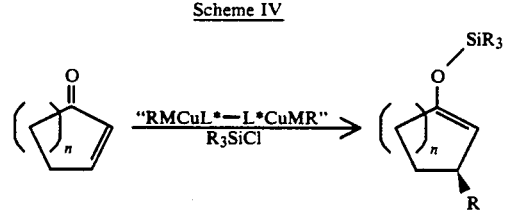

The present invention is useful in the synthesis of single enantiomers of a wide variety of chiral organic compounds including ketones, aldehydes, esters, amides, lactones, lactams, alcohols, amines and hydrocarbons. It is particularly useful in the synthesis of single enantiomers of physiologically active substances such as drugs, vitamins, and insect pheromones where the presence of undesired stereoisomers may introduce unwanted physiological side effects and where it is economically advantageous to produce pure enantiomers.

EXAMPLE 1

Synthesis of the Preferred Amine
(S)-N-Methyl-1-phenyl-2-(1-piperidinyl)-1-ethanamine A solution of (S)-carbobenzoxyphenylglycine (40.6 g, 0.142 mol) in THF (350 mL was treated with 4-methylmorpholine (14.4 g, 0.142 mol) and iso-butylchloroformate (19.4 g, 0.142 mol) at −15° C. with stirring for 5 min. A solution of piperidine (12.1 g, 0.142 mol) was added with stirring to the reaction mixture at −15° c. resulting in the formation of a white solid. The reaction was stirred for 1 hour at −15° C. and then warmed to ca. 0° C. The reaction mixture was concentrated and dissolved in ethyl acetate (650 mL) and water (100 mL). The ethyl acetate layer was washed with 1N HCl (2×250 mL), water (1×100 mL), 5% NaHCO$_3$ (2×250 mL), and water (1×250 mL) followed by saturated NaCl (1×200 mL). The ethyl acetate layer was dried (Na$_2$SO$_4$, anh.) and concentrated to afford the crude carbobenzoxyamide as an oil (47.2 g, 0.134 mol, 94%). The product will usually crystallize on standing. It can be purified by preparative HPLC (hexanes/ethyl acetate=3/1) or by recrystallization from ethyl acetate-hexanes giving white crystals (mp 76.5°–77.5° C.). The enantiomeric purity of the product can be improved by recrystallization from ethyl acetate-hexanes and can be monitored by analytical HPLC using a Daicel Chiracel OD column (10% iso-propanol-hexane).

The crude carbobenzoxyamide (47.2 g, 0.134 mol) was dissolved in dry THF (250 mL) and added dropwise to a suspension of LiAlH$_4$ (40.8 g, 1.08 mol) in THF (350 mL) at 0° C. under an Ar atmosphere. The suspension was refluxed for 12 hr. The suspension was carefully treated with THF (300 mL) and water (50 mL) at 0° C. followed by 50 mL of 15% NaOH and 30 mL of water. After filtration of the resulting suspension, the solid residue was washed with 200 mL of THF. The THF and filtrate were combined and concentrated to afford an oily residue. The oily residue was dissolved in 1N HCl (280 mL), the solution was washed with ether (400 mL×2) and the ether extract was discarded. The water layer was brought to pH≧12 with 5N KOH followed by extraction with ether (400 mL×2). The ether layer was dried (MgSO$_4$) and concentrated to afford 25.0 g of crude amine. The amine was purified by vacuum distillation (98°–100° C., 0.05 mmHg) to afford 19.9 g (0.091 mol, 68% yield) of product. The enantiomeric purity of the product was monitored by analytical HPLC using a Daicel Chiracel OD column (2% isopropanol-hexane). $[\alpha]_D = +108$ (c=1.79, chloroform), IR (neat): 3329, 2934, 2787, 1440, 1109, 701 cm$^{-1}$, $^1$H NMR (200 MHz, CDCl$_3$) d 1.40 (m, 2, C—CH$_2$—C), 1.58 (m, 4, C—CH$_2$—C), 2.37 (s, 3, CH$_3$—N), 2.20–2.65 (m, 7, —CH$_2$—N and NH), 3.60 (dd, 1, benzyl), 7.35 (m, 5, phenyl), Mass spectrum (m/e), 219 (M+1), 188, 120, 98.

Anal. Calcd for C$_{14}$H$_{22}$N$_2$: C, 77.01; H, 10.16; N, 12.83. Found: C, 77.24; H, 10.23; N, 12.94.

EXAMPLE 2

(S)-N-methyl-1-phenyl-2-(1-piperidinyl)ethanamine (139.0 mg, 0.638 mmol) was dissolved in dimethyl sulfide (4 mL) and n-butyl lithium (2.5M in hexanes, 0.255 mL, 0.638 mmol) was added to the solution at −65° C. The solution was stirred for 5 min at −65° C., gradually warmed to 0° C. and stirred for 10 min at 0° C. To a second flask was added CuI (81 mg, 0.425 mmol) and 4 mL of dimethyl sulfide. This solution was cooled to −40° C. and treated with n-butyl lithium (0.17 mL, 0.425 mmol). The lithium amide solution in the first flask was cooled to −35° C. and added via canula to the solution of n-BuCu in the second flask. The resulting solution was stirred for 15 min at −35° C., for 10 min at −30° C., and cooled to −78° C. After 30 min, 2-cyclohexenone (40.8 mg, 0.425 mmol) was added slowly at −78° C. The reaction mixture was quenched after 1 hr by adding 4N NH$_4$Cl (15 mL) at −78° C. and extracted with ether (15 mL). The extract was washed with 1N HCl (15 mL), dried (Na$_2$SO$_4$) and concentrated. The oily residue was purified by column chromatography on silica gel (10:1=hexanes/ethyl acetate) to afford (S)-3-n-butylcyclohexanone (37.1 mg, 57% chemical yield, 83% ee, $[\alpha]_D = -7.10$ (c=1.00, toluene)).

EXAMPLE 3

(S)-N-methyl-1-phenyl-2-(1-piperidinyl)ethanamine (348.4 mg, 1.60 mmol) was dissolved in ether (12 mL) and n-butyl lithium (2.5M in hexanes, 0.61 mL, 1.53 mmol) was added to the solution at −65° C. The solution was stirred for 5 min at −65° C., gradually (for 20 min) warmed to 0° C. and stirred for 10 min at 0° C. To a second flask was added CuI (254 mg, 1.33 mmol) and 10 mL of diethyl ether. This solution was cooled to −40° C. and treated with n-butyl lithium (0.51 mL, 1.28 mmol). The solution in the first flask was cooled to −35° C. and added via canula to the solution of n-BuCu in the second flask. The resulting solution was stirred for 15 min at −35° C., for 10 min at −30° C., and cooled to −78° C. After 30 min, 2-cycloheptenone (141 mg, 1.28 mmol) was added slowly at −78° C. The reaction mixture was quenched after 1 hr by adding 4N NH$_4$Cl (15 mL) at −78° C. and extracted with ether (20 mL). The extract was washed with 1N HCl (15 mL), dried (Na$_2$SO$_4$) and concentrated. The oily residue was purified by column chromatography on silica gel (10:1=hexanes/ethyl acetate) to afford (S)-3-n-butylcycloheptanone (136 mg, 63% chemical yield, 96% ee, $[\alpha]_D = -33.0$ (c=3.2, chloroform)).

EXAMPLE 4

(S)-N-[1,6-Hexanediyl]-N,N'-dimethyl-2-phenyl-1,2-ethanediamine (149.7 mg, 0.365 mmol) was dissolved in ether (5 mL) and n-butyl lithium (2.5M in hexanes, 0.29 mL, 0.725 mmol) was added to the solution at −65° C. The solution was stirred for 5 min at −65° C., warmed to 0° C. and stirred for 10 min at 0° C. To a second flask was added CuI (116 mg, 0.61 mmol) and 4 mL of diethyl ether. This solution was cooled to −40° C. and treated with n-butyl lithium (0.24 mL, 0.60 mmol). The solution in the first flask was cooled to −35° C. and added via canula to the solution of n-BuCu in the second flask. The resulting solution was stirred for 15 min at −35° C., for 10 min at −30° C., and cooled to −78° C. After 30 min, 2-cyclohexenone (57.6 mg, 0.60 mmol) was added slowly at −78° C. After 1 hr, the internal standard for gas chromatography, dodecane (138 ul), was added to the reaction mixture, which was quenched by adding 4N NH$_4$Cl (15 mL) at −78° C. and extracted with ether (20 mL×1). The extract was washed with 1N HCl (15 mL×1), dried (Na$_2$SO$_4$) and concentrated. (58% yield, 55% ee) The chemical yield was estimated by GC using the internal standard dodecane. The enantiomeric excess was determined by reacting the product with (+)-diethyl tartrate and p-toluenesulfonic acid to form diasteromeric ketals and anylzing the product mixture by capillary GC.

EXAMPLE 5

(S)-N-methyl-1-phenyl-2-(1-piperidinyl)ethanamine (360.0 mg, 1.65 mmol) was dissolved in ether (12 mL) and n-butyl lithium (2.5M in hexanes, 0.66 mL, 1.65 mmol) was added to the solution at $-65°$ C. The solution was stirred for 5 min at $-65°$ C., warmed to $0°$ C. and stirred for 10 min at $0°$ C. To a second flask was added CuI (262 mg, 1.38 mmol) and 10 mL of diethyl ether. This solution was cooled to $-40°$ C. and treated with n-butyl lithium (0.55 mL, 1.38 mmol). The solution in the first flask was cooled to $-35°$ C. and added via canula to the solution of n-BuCu in the second flask. The resulting solution was stirred for 15 min at $-35°$ C., for 10 min at $-30°$ C., and cooled to $-78°$ C. After 5 min, chlorotrimethylsilane (0.437 mL, 3.44 mmol) was added and stirred for 15 min. 2-Cyclopentenone (112.8 mg, 1.38 mmol) was added slowly at $-78°$ C. to the reaction mixture, which was quenched after 1 hr by adding 4N NH$_4$Cl (15 mL) at $-78°$ C. and extracted with ether (20 mL). The extract was washed with 1N HCl (15 mL), dried (Na$_2$SO$_4$) and concentrated. The oily residue was purified by column chromatography on silica gel (5:1=pentane/ether) to afford (S)-3-n-butylcyclopentanone (98.7 mg, 51% chemical yield, 44% ee, $[\alpha]_D = -54.4$ (c=3.00, benzene)).

EXAMPLE 6

(S)-N-methyl-1-phenyl-2-(1-piperidinyl)ethanamine (361.1 mg, 1.66 mmol) was dissolved in ether (12 mL) and n-butyllithium (2.5M in hexanes, 0.66 mL, 1.65 mmol) was added to the solution at $-65°$ C. The solution was stirred for 5 min at $-65°$ C., warmed to $0°$ C. and stirred for 10 min at $0°$ C. To a second flask was added CuI (263 mg, 1.38 mmol) and 10 mL of diethyl ether. This solution was cooled to $-40°$ C. and treated with n-butyl lithium (0.55 mL, 1.38 mmol). The solution in the first flask was cooled to $-35°$ C. and added via canula to the solution of n-BuCu in the second flask. The resulting solution was stirred for 15 min at $-35°$ C., for 10 min at $-30°$ C., and cooled to $-78°$ C. After 30 min, the ether (1 mL) solution of 4-phenyl-3-buten-2-one (201.5 mg, 1.38 mmol) was added slowly at $-78°$ C. The reaction mixture was stirred for 1 hr at $-78°$ C. and warmed to $-20°$ C. The reaction was quenched by adding 4N NH$_4$Cl (15 mL) at $-20°$ C. and extracted with ether (20 mL). The extract was washed with 1N HCl (15 mL), dried (Na$_2$SO$_4$) and concentrated. The oily residue was purified by column chromatography on silica gel (8:1=hexanes/ethyl acetate) to afford (+)-4-phenyl-2-octanone (95.6 mg, 34% chemical yield, 2% ee, $[\alpha]_D = 0.06$ (c=5.00, chloroform)).

EXAMPLE 7

(S)-N-methyl-1-phenyl-2-(1-piperidinyl)ethanamine (345.0 mg, 1.58 mmol) was dissolved in ether (12 mL) and n-butyllithium (2.5M in hexanes, 0.63 mL, 1.575 mmol) was added to the solution at $-65°$ C. The solution was stirred for 5 min at $-65°$ C., warmed to $0°$ C. and stirred for 10 min at $0°$ C. To a second flask was added CuI (251 mg, 1.32 mmol) and 10 mL of diethyl ether. This solution was cooled to $-40°$ C. and treated with n-butyl lithium (0.53 mL, 1.323 mmol). The solution in the first flask was cooled to $-35°$ C. and added via canula to the solution of n-BuCu in the second flask. The resulting solution was stirred for 15 min at $-35°$ C., for 10 min at $-30°$ C., and cooled to $-78°$ C. After 30 min, 5-methyl-2-cyclohexenone (290 mg, 2.64 mmol) was added slowly at $-78°$ C. The reaction mixture was quenched after 1 hr by adding 4N NH$_4$Cl (15 mL) at $-78°$ C. and extracted with ether (20 mL). The extract was washed with 1N HCl (15 mL), dried (Na$_2$SO$_4$) and concentrated. The oily residue was purified by column chromatography on silica gel (ether/pentane=⅛ followed by ether/pentane=1/5) to afford (S,S)-3-n-butyl-5-methylcyclohexanone (176 mg, 79% chemical yield, 39% ee, $[\alpha]_D = 5.5$ (c=1.00, benzene)) and (R)-5-methyl-2-cyclohexenone (78 mg, 54% chemical yield, 28% ee, $[\alpha]_D = 22.8$ (c=4.00, acetone)).

EXAMPLE 8

(S)-5,8-Dimethyl-3-phenyl-2,5,8-triazanonane (118 mg, 0.51 mmol) was dissolved in dimethyl sulfide (4 mL) and n-butyl lithium (2.5M in hexanes, 0.20 mL, 0.51 mmol) was added to the solution at $-65°$ C. The solution was stirred for 5 min at $-65°$ C., warmed to $0°$ C. and stirred for 10 min at $0°$ C. To a second flask was added CuI (64 mg, 0.34 mmol) and 4 mL of dimethyl sulfide. This solution was cooled to $-40°$ C. and treated with n-butyl lithium (0.13 mL, 0.34 mmol). The solution in the first flask was cooled to $-35°$ C. and added via canula to the solution of n-BuCu in the second flask. The resulting solution was stirred for 15 min at $-35°$ C., for 10 min at $-30°$ C., and cooled to $-78°$ C. After 30 min, 2-cyclohexenone (12.9 mg, 0.134 mmol) was added slowly at $-78°$ C. After 1 hr, the internal standard for gas chromatography, dodecane (30 ul), was added to the reaction mixture. The reaction was quenched by adding 4N NH$_4$Cl (10 mL) at $-78°$ C. and extracted with ether (20 mL). The extract was washed with 1N HCl (15 mL), dried (Na$_2$SO$_4$) and concentrated (100% yield, 71% ee). The chemical yield was estimated by GC using the internal standard dodecane. The enantiomeric excess was determined by reacting the product with (+)-diethyl tartrate and p-toluenesulfonic acid to form diastereomeric ketals and anylzing the product mixture by capillary GC.

EXAMPLE 9

(S)-N-methyl-1-phenyl-2-methoxy ethanamine (121 mg, 0.74 mmol) was dissolved in dimethyl sulfide (4 mL) and n-butyl lithium (2.5 M in hexanes, 0.29 mL, 0.74 mmol) was added to the solution at $-65°$ C. The solution was stirred for 5 min at $-65°$ C., warmed to $0°$ C. and stirred for 10 min at $0°$ C. To a second flask was added CuI (117 mg, 0.61 mmol) and 4 mL of dimethyl sulfide. This solution was cooled to $-40°$ C. and treated with n-butyl lithium (0.25 mL, 0.61 mmol). The solution in the first flask was cooled to $-35°$ C. and added via canula to the solution of n-BuCu in the second flask. The resulting solution was stirred for 15 min at $-35°$ C., for 10 min at $-30°$ C., and cooled to $-78°$ C. After 30 min, 2-cyclohexenone (58.59 mg, 0.610 mmol) was added slowly at $-78°$ C. After 1 hr, the internal standard for gas chromatography, dodecane (139 ul), was added to the reaction mixture, which was quenched by adding 4N NH$_4$Cl (10 mL) at $-78°$ C. and extracted with ether (20 mL). The extract was washed with 1N HCl (15 mL), dried (Na$_2$SO$_4$) and concentrated (92% yield, 68% ee). The chemical yield was estimated by GC using the internal standard dodecane. The enantiomeric excess was determined by reacting the product with (+)-diethyl tartrate and p-toluenesulfonic acid to form diastereomeric ketals and anylzing the product mixture by capillary GC.

We claim:

1. A chiral copper (I) complex of the formula R(L*)CuM wherein M is a metal ion selected from the group consisting of Li, Na, K, Cs and Rb, R is selected from the group consisting of aryl, alkyl and aralkyl and LH* is

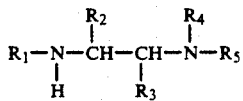

$R_1$ and $R_2$ are alkyl, aryl or aralkyl, $R_3$ is H, alkyl, aryl or aralkyl, $R_4$ and $R_5$ form, together with the nitrogen to which they are attached, a heterocyclic ring of 4-8 members including an additional hetero atom selected from a group consisting of oxygen and sulfur; the heterocyclic ring contains no more than 2 hetero atoms including the nitrogen atom to which the $R_4$ and $R_5$ are attached.

2. A chiral copper(I) complex of claim 1 wherein M is lithium.

3. A chiral copper(I) complex of claim 1 wherein for formula I, $R_1$ is a straight chain alkyl from 1 to 12 carbon atoms, $R_2$ is aryl, and $R_3$ is H.

4. A chiral copper(I) complex of claim 1 wherein $R_4$ and $R_5$ form a heterocyclic ring with the nitrogen to which they are attached form a heterocyclic moiety selected from the group consisting of piperidine, pyrrolidine, morpholine, perhydroazepine and perhydroazocine.

5. A chiral copper(I) complex of claim 1 wherein $R_1$ is methyl, $R_2$ is phenyl, $R_3$ is hydrogen, and $R_4$ and $R_5$, together with the nitrogen form a piperidine moiety.

* * * * *